(12) United States Patent
Werth

(10) Patent No.: US 7,090,257 B2
(45) Date of Patent: Aug. 15, 2006

(54) BARB CLAMP

(75) Inventor: Albert A. Werth, Kewadin, MI (US)

(73) Assignee: Twin Bay Medical, Inc., Traverse City, MI (US)

( * ) Notice: Subject to any disclaimer, the term of this patent is extended or adjusted under 35 U.S.C. 154(b) by 395 days.

(21) Appl. No.: 10/414,642

(22) Filed: Apr. 16, 2003

(65) Prior Publication Data

US 2003/0193190 A1 Oct. 16, 2003

Related U.S. Application Data

(60) Provisional application No. 60/389,844, filed on Jun. 19, 2002, and provisional application No. 60/373,064, filed on Apr. 16, 2002.

(51) Int. Cl.
*F16L 33/00* (2006.01)

(52) U.S. Cl. .................. 285/243; 285/3; 285/257; 285/255; 285/322

(58) Field of Classification Search ............ 285/3, 285/4, 148.13, 148.14, 148.17, 148.2, 243, 285/257, 322, 324, 255
See application file for complete search history.

(56) References Cited

U.S. PATENT DOCUMENTS

| | | | |
|---|---|---|---|
| 1,390,564 A | | 9/1921 | Knorr |
| 2,868,564 A | | 1/1959 | Arras |
| 3,606,396 A | * | 9/1971 | Prosdiedimo et al. ........ 285/243 |
| 3,724,882 A | * | 4/1973 | Dehar ........................ 285/243 |
| 3,868,130 A | * | 2/1975 | Schwertner et al. ........ 285/243 |
| 4,205,417 A | * | 6/1980 | Mackal .......................... 285/3 |
| 4,880,414 A | | 11/1989 | Whipple |
| 4,890,866 A | | 1/1990 | Arp |
| 4,932,689 A | * | 6/1990 | Bradley ....................... 285/255 |
| 5,074,600 A | | 12/1991 | Weinhold |
| 5,140,738 A | * | 8/1992 | Pinkerman, Jr. ............ 285/243 |
| 5,141,263 A | * | 8/1992 | Varden ....................... 285/243 |
| 5,240,289 A | | 8/1993 | Gottling |
| 5,584,513 A | | 12/1996 | Sweeny et al. |
| 5,882,047 A | | 3/1999 | Ostrander et al. |
| 5,909,902 A | | 6/1999 | Seabra |
| 5,984,378 A | | 11/1999 | Ostrander et al. |
| 6,155,610 A | | 12/2000 | Godeau et al. |

* cited by examiner

*Primary Examiner*—Aaron Dunwoody
(74) *Attorney, Agent, or Firm*—Young & Basile, P.C.

(57) ABSTRACT

A plastic barb clamp provides leakproof connection of a flexible tube in a barb fitting. The barb clamp includes a collet and a sleeve. The barb clamp is configured to fit snugly within the tube. The collet is slid over the tube. Annular retainers on the interior surface of the collet fit tightly around the tube and under an expanded portion of the barb fitting. The sleeve is then slid over the collet. As the sleeve moves over the collet, tangs on the collet are pushed radially inwardly into the tube and barb fitting. The exterior surface of the collet has radial projections or expanded diameter portions for locking with the sleeve. The sleeve has an annular projection or a reduced diameter portion on the interior surface of the sleeve to correspond to the exterior surface of the collet to provide a secure lock between the collet and sleeve. To properly orientate the sleeve relative to the collet, the sleeve and collet can be molded as one piece, wherein the sleeve and collet are connected by thin, frangible pieces of plastic.

20 Claims, 9 Drawing Sheets

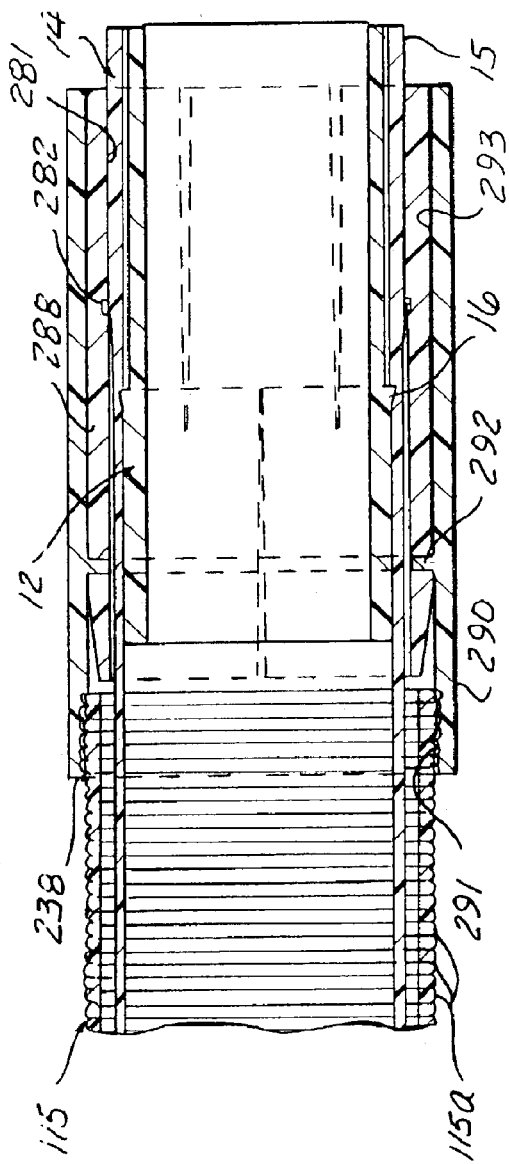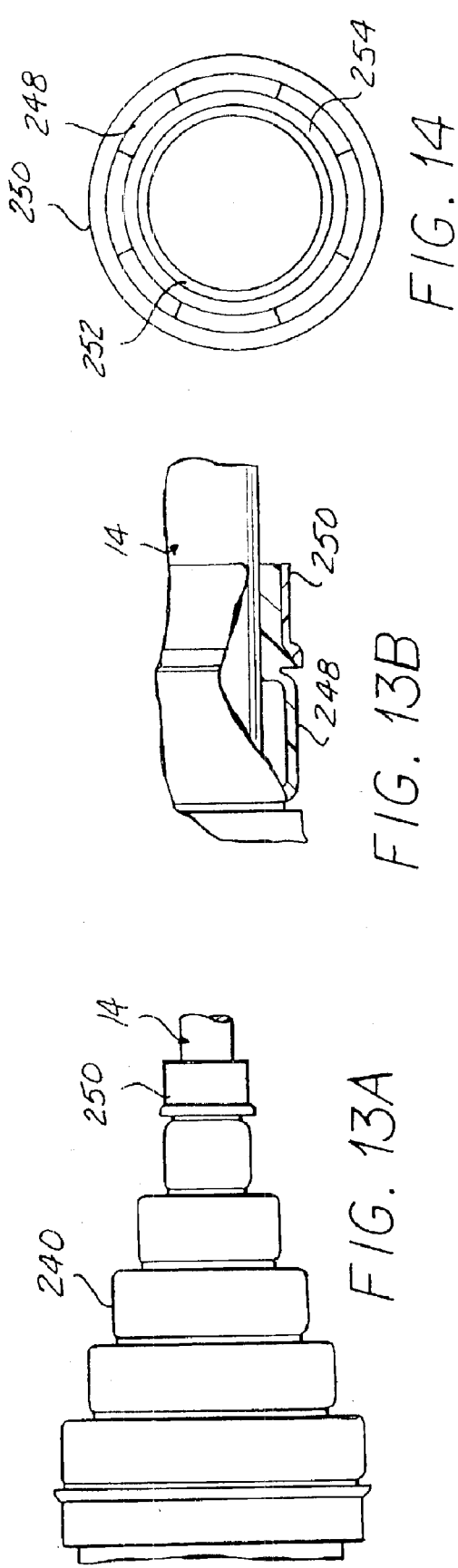

BARB CLAMP

This application claims priority of Provisional Patent Application Ser. No. 60/373,064 filed on Apr. 16, 2002 and Provisional Application Ser. No. 60/389,844 filed on Jun. 19, 2002.

FIELD OF THE INVENTION

The present invention relates to a fastening device for a tubular body.

BACKGROUND OF THE INVENTION

The transfer of fluid through flexible tubing is widely used in various environments. Ultimately, the flexible tubing is connected to the source of the gaseous or liquid fluid, the delivery site of the fluid, or to another flexible tubing. At the ends of the flexible tubing, it is necessary to provide a secure and leak proof connections. Although these requirements are necessary in all environments using flexible tubing, it is critical in the medical and pharmaceutical fields. In the medical and pharmaceutical fields flexible tubing and associated connections are used for luer fittings, quick connects, or sanitary fittings such as used in blood pumps, oxygen concentrators, sleep apnea equipment, medical transport containers, IV bags, etc. Currently the flexible tubing in these areas use cable ties. In the automotive and other industrial environments, the flexible tubing is connected to a barb fitting by hose clamps. Both of these means of connection demonstrate poor pull off strength and provides an inherent leak path.

SUMMARY OF THE INVENTION

The present invention is a barb clamp used for joining a flexible tube and a barbed fitting. The fitting is used in numerous applications, and especially in the medical and pharmaceutical fields such as sleep apnea equipment, medical transport containers, and IV bags. The barb clamp of the present invention replaces the cable tie which demonstrates poor pull off strength and inherent leak path.

In once aspect of the invention, the barb clamp includes a cylindrical collet engageable over one end of the barb fitting and tube. The collet has resilient means for radially contracting around the tube for forming a tight fit. The barb clamp further includes a cylindrical sleeve having a through center aperture for receiving the collet, wherein the collet has an exterior surface and an annular groove in the exterior surface. The sleeve has an interior surface with an annular projection configured and positioned for disposition in the annular groove of the collet, wherein the collet also has an annular lip defining a stop at one end for terminating movement of the sleeve over the collet.

In another aspect of the invention, the exterior surface of the collet includes a thread molded on a portion thereof to facilitate threading into the sleeve having a corresponding thread formed on its inner surface.

In yet another aspect of the invention, the collet and sleeve are integrally molded together, wherein the collet is connected to the sleeve at thin frangible pieces of plastic.

In another aspect of the invention, the collet is integrally molded to a boot having a corrugated exterior portion and the annual lip is located between the collet and the boot, wherein the annular lip may include micro slits formed therein.

In another aspect of the invention, the collet has a radial, bulbous exterior portion; and the sleeve has a reduced inner bore positioned for tightly receiving the radial bulbous exterior portion of the collet to provide superior holding strength for the tube and barb fitting.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIG. 12 is sectional view of a sleeve and collet for a corrugated covering;

FIG. 13a is a side elevational view of a boot seal with an integral collet and a sleeve configured for the boot;

FIG. 13b is a portion of a sectional view of the boot seal with the integral collet and sleeve of FIG. 13a;

FIG. 14 is a sectional view of FIG. 13b taken along lines 14—14;

DETAILED DESCRIPTION OF THE PREFERRED EMBODIMENT

Figure 1:
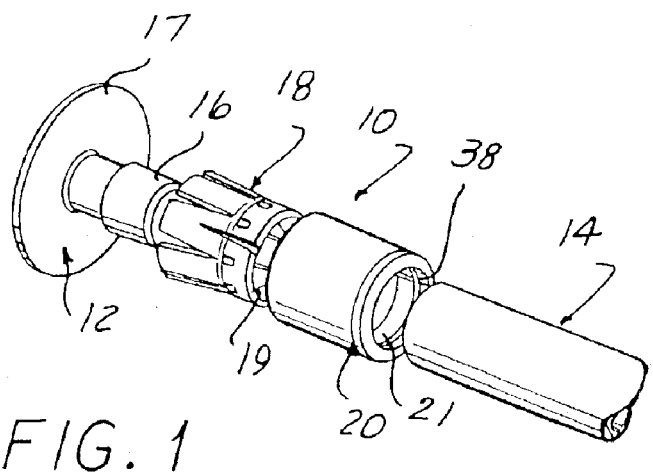
FIG. 1 is a perspective view of one embodiment of the barb clamp, including a collet and sleeve engagement.
Figure 2:
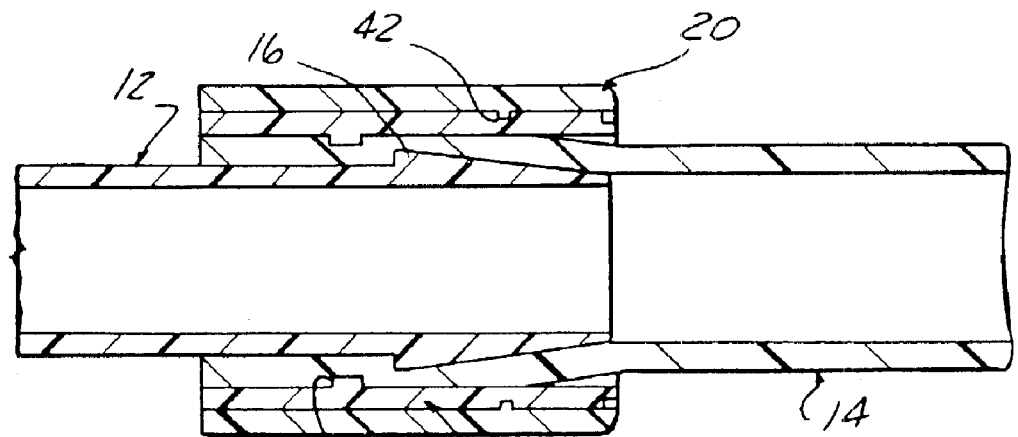
FIG. 2 is a sectional view of the barb clamp as engaged over a tube and barbed fitting.

FIGS. 1 and 2 show the barb clamp 10 of the present invention for coupling a barbed fitting 12 and a tube 14. The barbed fitting 12 is made of a nonmetal material which allows it to be heat welded to a propolene or ethelene medical or pharmaceutical bag. The barb fitting 12 may encompass different configurations but will generally include an expanded end 16 for a snug connection into a flexible tube 14 preferably made of an FDA approved silicon, TPE, TPR Ect. The barbed fitting 12 may also include a flanged portion 17 which defines a stop for the connector 10.

The connector 10 includes a collet 18 and a sleeve 20. The collet 18 is an essentially annular member having a through aperture 19 for receiving the end of a tube 14 therein. The sleeve 20 is also an annular member with a through aperture 21 for receiving the end of the tube 14 as well as having a diameter for also receiving the collet 18 therein. The collet 18 and sleeve 20 can be made of an FDA approved material. The material should be resilient, such as polypropylene. Preferably the collet 18 is made of acetal; and sleeve 20 is made of polycarbonate.

Figure 3:
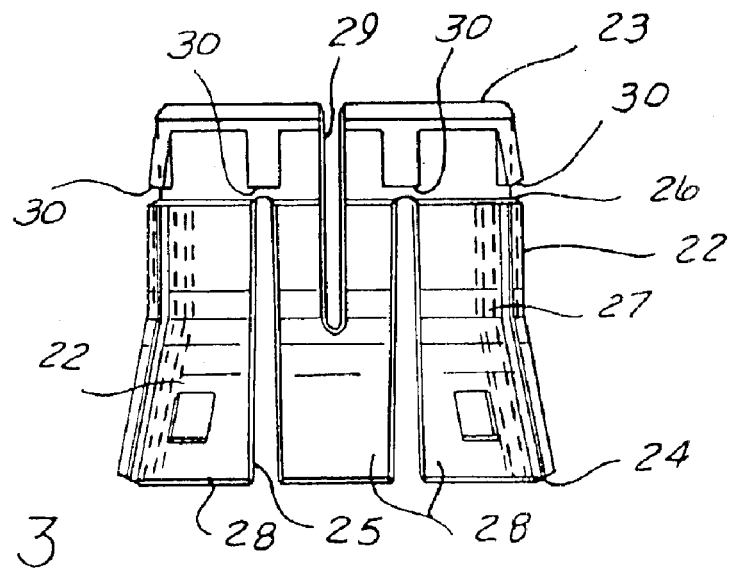
FIG. 3 is an elevational view of the collet.
Figure 4:
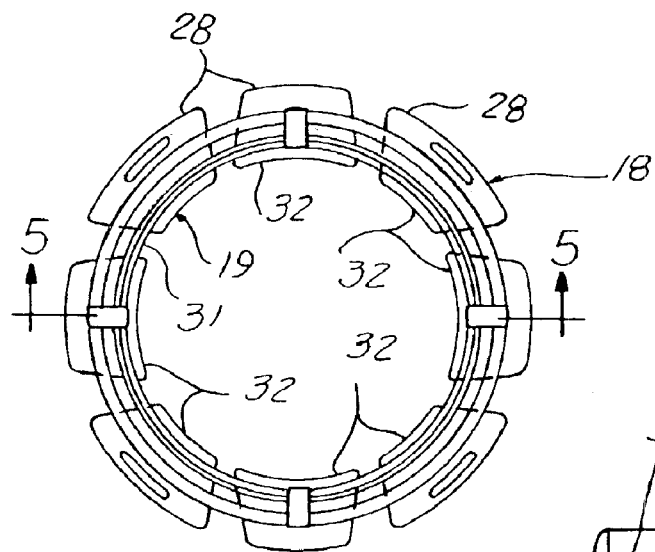
FIG. 4 is an end view of the collet.
Figure 5:
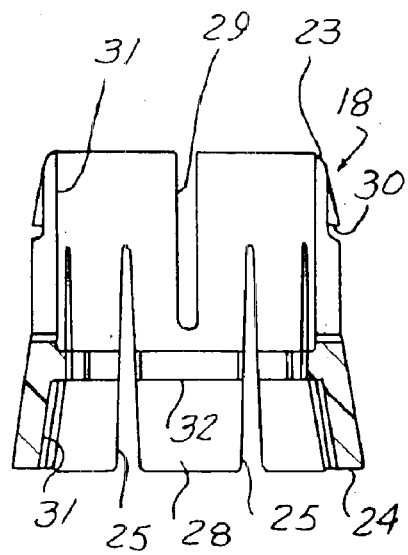
FIG. 5 is a sectional view of the collet taken along lines 5—5 of FIG. 4.

Looking at FIGS. 3–5 the collet 18 has an exterior surface 22 providing resilient means for radially contracting around the tube 14. The collet 18 has a first end 23 forming a discontinuous annular ring. Along the exterior surface 22 and adjacent to the first end 23 is an annular groove 26. Moving toward the second end 24 and beyond the annular groove 26, the collet forms eight resilient tangs 28. The tangs 28 radially flare out or expand slightly at the second end 24 of the collet 18. The tangs 28 begin to flare approximately at the mid section 27 of each tang 28. The tangs 28 are formed by narrow through slots 25 extending from the second end 24 and terminating at the annular groove 26. A small ledge 30 projects above each termination point of the narrow through slots 25. The small ledges 30 provide added strength to the collet and also provide a stop means for the sleeve 20, as will be discussed hereinafter. The eight tangs 28 form a resilient seal which allow the tangs to contract around a tubular member. Between every other tang 28a through slot 29 extends from the first end 23 to the midsection 27 of the associated tang 28. The through slots 29 provide resiliency to the first end 23 of the collet 18 without sacrificing durability. The interior surface 31 of the collet 18 is essentially smooth except for a shelf 32 equally positioned on each tang 28 at the mid-section 27 for reasons to be discussed further.

Figure 6:
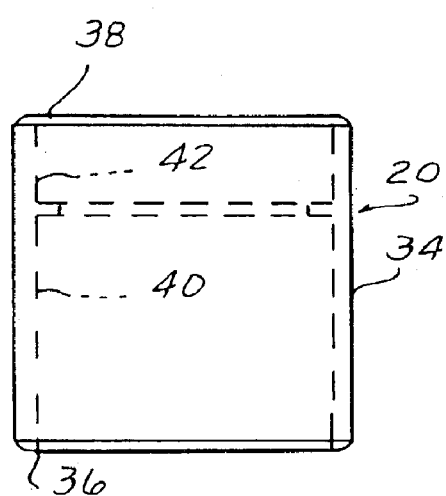
FIG. 6 is an elevational view of the sleeve.
Figure 7:
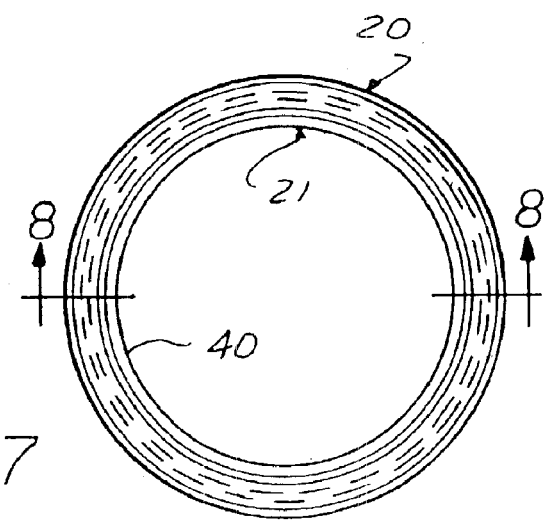
FIG. 7 is an end view of the sleeve.
Figure 8:
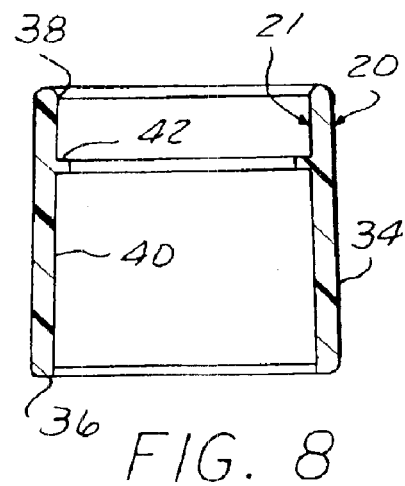
FIG. 8 is a sectional view of the sleeve taken along lines 8—8 of FIG. 7.

The sleeve 20 is shown in FIGS. 6–8. The sleeve 20 has a smooth exterior annular surface 34. The sleeve 20 has a first or bottom end 36 forming a flat base. The interior surface 40 has a slight outward taper starting at the second of top end 38 of the sleeve 20 and increasing in size to the bottom end 36. The interior surface 40 is essentially smooth throughout the length except for an annular projection 42 that extends from the inner surface 40. The annular projection 42 is sized and positioned on the sleeve 20 for disposition within the annular groove 26 of the collet 18 when the connector 10 is engaged. Therefore, the annular projection 42 is positioned proximate to the second or top end 38 of the sleeve 20.

The barb clamp 10 is connected with the barbed fitting 12 and tube 14 as discussed hereinafter and as shown in FIGS. 1 and 2. The sleeve 20 is first placed over the free end of the tube 14 so that the second or top end 38 of the sleeve 20 is spaced furthest away from the tube end when the sleeve is on the tube 14. The collet 18 is then placed on the tube 14 so that the first end 23 of the collet 18 is closest to the sleeve 20. The expanded end 16 of the barbed fitting 12 is then placed into the tube 14. The expanded end 16 of the barbed fitting 12 is sized for being received within the interior of the tube 14. The collet 18 is then slid over the tube expanded end 16 of the barbed fitting 12, now within tube 14. The shelves 32 located on the interior surface 31 of the collet 18 fit snugly around the tube 14 and under the expanded end 16 of the barb fitting 12. The shelves 32 on the collet 18 define a retainer around the barb fitting 12. The sleeve 20 is then slid over the collet 18 such that the first or bottom end 36 of the sleeve 20 initially encounters the first end 23 of the collet 18. As the sleeve 20 moves over the collet, the tangs 28 on the collet are pushed inwardly into the tube 14 and barbed fitting 12, so that the annular shelves 32 of the collet 18 are pressed inwardly into the tube 14 and barbed fitting 12 to provide a tight seal therebetween and lock the annular shelves 32 under the barb 16. The sleeve 20 continues over the collet 18 until the annular projection 42 on the interior surface 40 of the sleeve 20 sits within the annular groove 26 of the collet 18. The small ledges 30 on the interior surface 31 of the collet 18 provides a stop and lock to prevent the annular projection 42 from moving out of annular groove 26. The barb clamp 10 can then only be removed with the aid of a tool so that disconnection and leakages are prevented. The barb clamp provides a retainer system with a full 360° radial compression on the barb fitting 12 and tube 14.

Figure 9:
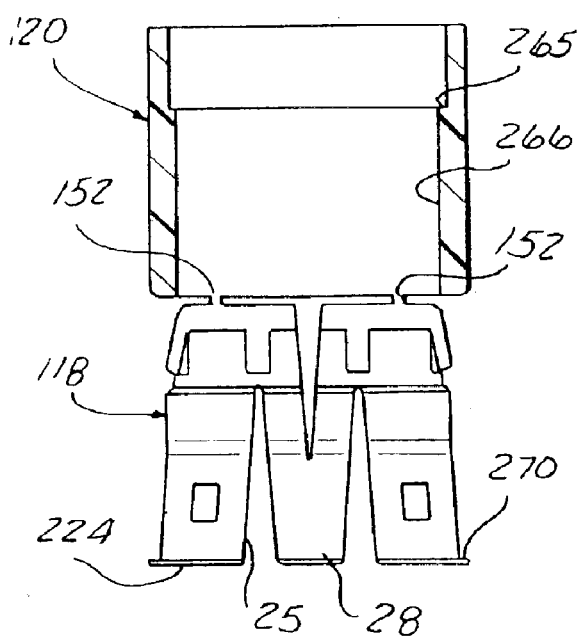
FIG. 9 is a sectional view of the sleeve and collet molded as a single unit.
Figure 15:
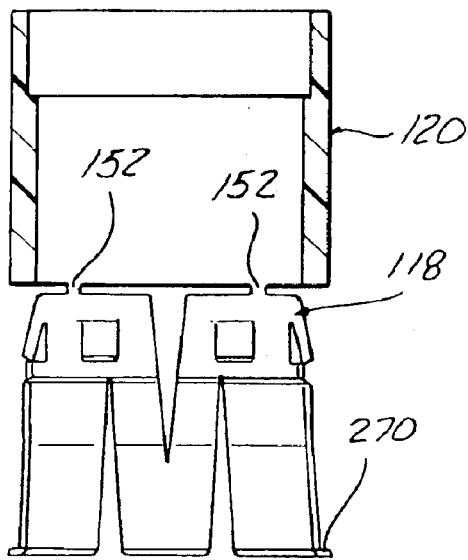
FIG. 15 is a sectional view of the sleeve and collet molded as a single unit.

As an alternative, the sleeve 120 and collet 118 (FIGS. 9, 15 and 16) may be molded as a single unit with multiple thin webs of plastic or frangible pieces of plastic 152 that keep the two components (sleeve 120 and collet 118) joined together until final assembly (not shown). During the final assembly of the sleeve 120 and collet 118 to the barb fitting and tube (not shown), the multiple thin webs or frangible pieces of plastic 152 break away allowing the sleeve 120 and collet 118 to lock together. This feature facilitates automatic loading of the barb clamp device and further prevents improper orientation of the sleeve 120 and collet 118 during the final assembly. An annular lip or stop 270 may radially extends from the second end 224 of the collet 118. The annular lip or stop 270 defines a stop means for limiting the movement of the sleeve 120 over the collet 118.

Figure 16:
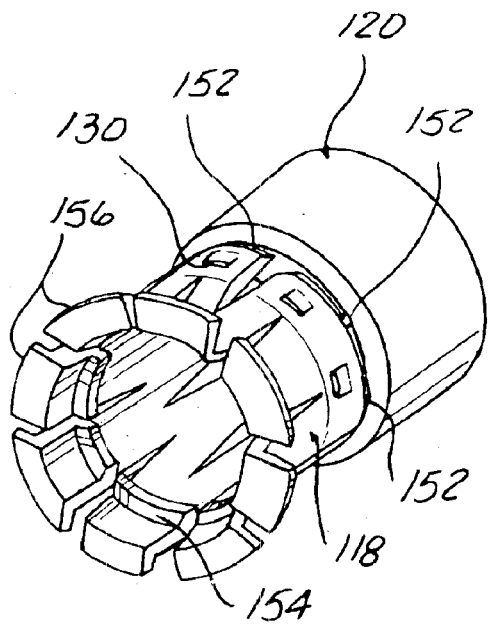
FIG. 16 is a perspective view of the single molded piece sleeve and collet combination shown in FIG. 15.
Figure 17A:
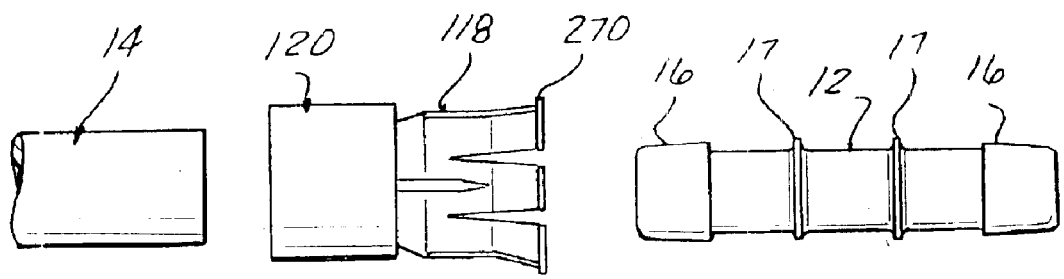
FIGS. 17a–c are side elevational views of a series of installation steps to install the single molded piece sleeve and collet combination onto a tube and a barbed connector.
Figure 17B:
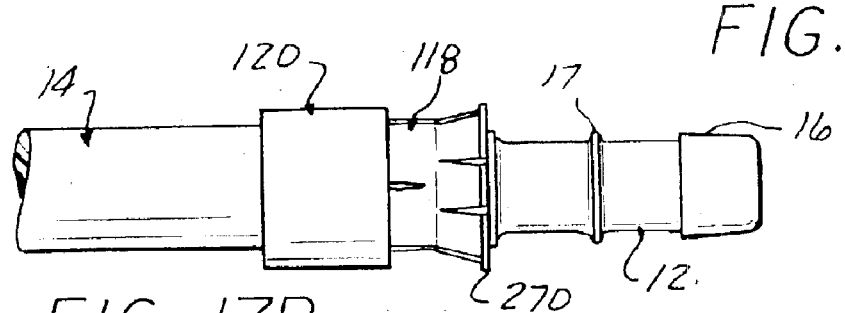
Figure 17C:
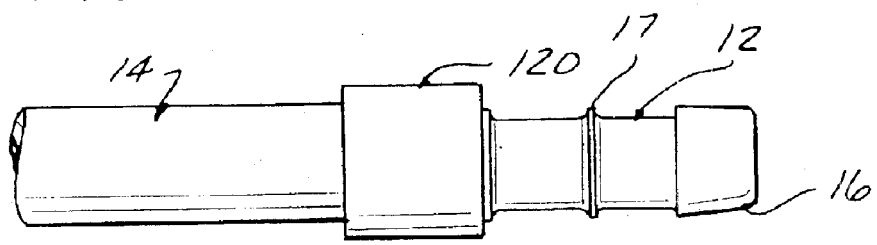

FIG. 16 also shows the sleeve 120 and collet 118 molded as a single unit with multiple plastic frangible pieces 152 to keep the two components (sleeve and collet) joined together until final assembly. The embodiment in FIG. 16 also shows the retainer ring 154 and the individual locking fingers 156 that encircle the base of the collet 118. When the collet 118 is assembled into the sleeve 120, the locking fingers 156 are compressed so that the internal retainer ring 154 is essentially continuous without gaps to secure or mount an annular projection (not shown in FIG. 10) within the sleeve 120. The annular projection in the sleeve 120 of FIG. 16 is the same as that shown in FIGS. 2 and 6. The retainer ring 154 provides a 360° compression around the tube. The locking ramps or ledges 130 click into a final lock position with the annular projection 42 of the sleeve at final assembly. FIGS. 17a–17c show the series of steps to assemble the combination collet and sleeve of FIGS. 15 and 16. This feature facilitates automatic loading of the retainer system and further prevents improper orientation of the sleeve 120 and collet 118 during the final assembly.

Figure 10:
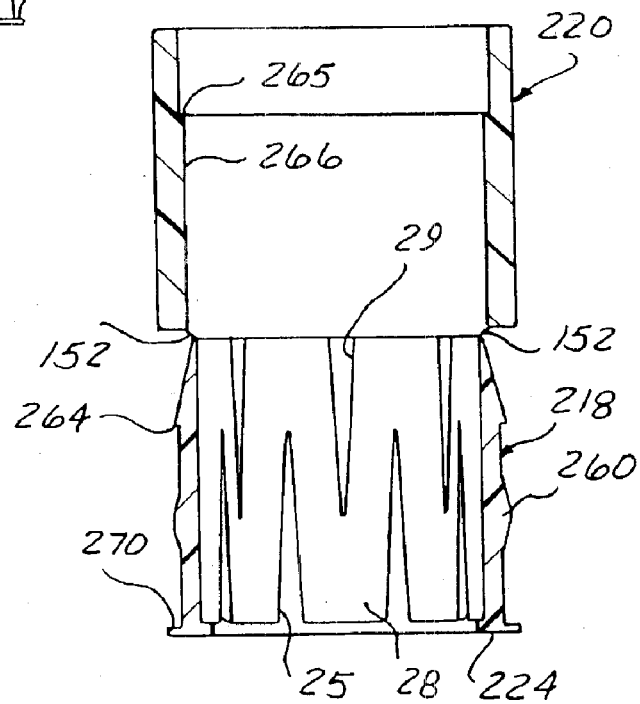
FIG. 10 is a sectional view of another embodiment sleeve and collet in the unassembled portion, having a protective feature for a barb fitting.
Figure 11:
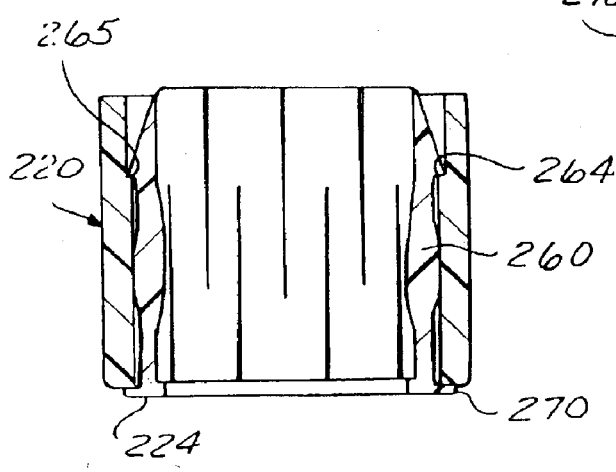
FIG. 11 is a sectional view of the sleeve and collet in FIG. 10 assembled.

Another alternative, as shown in FIGS. 10 and 11, of the sleeve 220 and collet 218 protects barb fittings 12 used in certain specific applications. The collet 218 is reconfigured to have a bulbous outer surface 260 to grip the inner surface 266 of the sleeve 220. The collet 218 also includes an annular lip or stop 270 along the lower edge 224 to act as a stop for the sleeve 220 upon assembly. The collet 218 also includes a small annular ledge 264 to lock onto a shelf 265 formed by a reduced counterbore section 266 of the sleeve 220 upon assembly. The sleeve 220 is also connected to the collet 218 by small frangible pieces of plastic 152. To protect the barb fitting (not shown), the collet 218 does not include the interior shelves 32 shown in FIG. 2. However, the features of the bulbous surface 260 and the annular lip 270 on the collet 218 and corresponding reduced counterbore 266 on the sleeve 220 respectively provide superior holding strength for the tube and barb fitting. The elimination of the interior shelves of the collet 218 is especially beneficial for small radius barb fittings having small barbs (approximately 1/16 inch) that can break easily.

Another embodiment for the barb clamp accommodates corrugated tube coverings as shown in FIG. 12. In certain environments and especially in automotive environments, a tube 14 may have a corrugated covering 115 to provide more flexibility and protection of the tube 14. An end portion 15 of the tube 14 will not have the corrugated covering 115. The sleeve 290 has a ribbed inner surface portion 291 at the top end 238 of the sleeve 290 to receive and grip ridges 115a of the corrugated covering 115 for applications that need a retainer for the tube 14 and corrugated covering 115 for protection. The sleeve 290 is placed over the end of the tube 14 and the corrugated covering 115 so that the ribbed inner surface portion 291 of the sleeve 290 is placed over the corrugated ridges 115a. The shelves 282 located on the interior surface 281 of the collet 288 fit snugly around the tube 14 and under the expanded end 16 of the barb fitting 12. The collet 288 is pressed inwardly into the tube 14 and the barbed fitting 12 to provide a tight seal therebetween and lock the annular shelf 282 under the barb 16. The annular projection 292 on the interior surface 293 of the sleeve 290 sits within the annular groove 286 of the collet 288. The ribbed inner surface portion 291 of the sleeve 290 further provides a grip for the ridges 115a of the corrugated covering 115. Other applications would use the retainer system to add the corrugation only to the sleeve 290.

A solution for sealing shaft boot covers 240 utilizing the collet and sleeve technology of the present invention is shown in FIGS. 13a, b and 14. The invention can be made in the standard manner with a sleeve 250 and collet 248 with a retaining ring 252 to provide 360° of radial compression. The boot clamp can also use a continuous bore 254 that is located at the end of the boot 240 with the integral collet 248 and a sleeve 250 to add compression. The boot lock can also be made with the a material process to create the retaining ring 252 inside the continuous bore to provide the ultimate seal.

Figure 18:
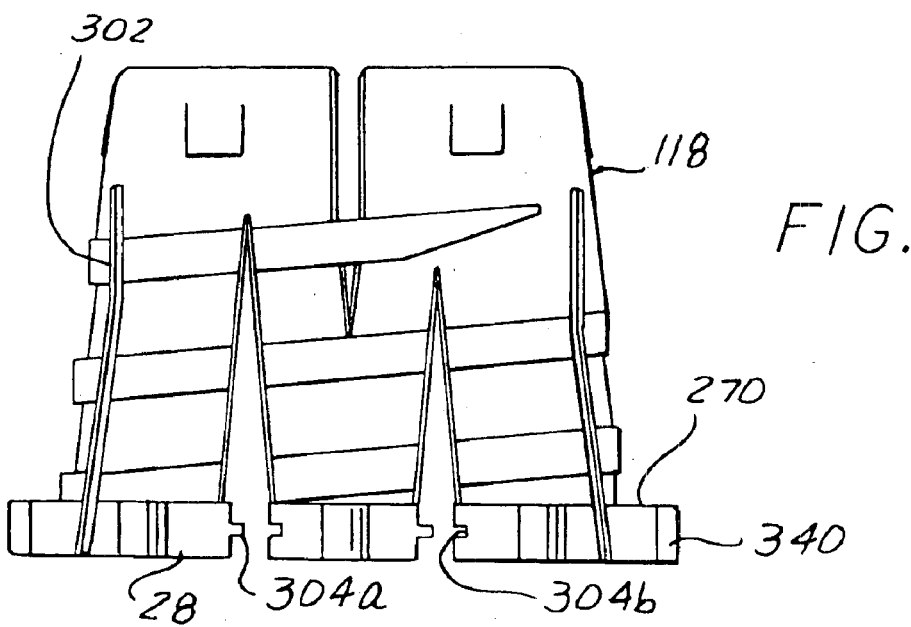
FIG. 18 is a side elevational view of a collet having interlocks and a threaded exterior surface.

FIG. 18 shows a collet 118 as shown and described in FIG. 10 but further including an outward circumferential thread 302 to facilitate installation into a sleeve. Although not shown, the sleeve may have a corresponding thread on the exterior surface to facilitate the threading installation of the collet 118 and sleeve over the tube and barb fitting. At the base of the collet 118 are interlocks 304a, b to prevent longitudinal shift of one portion of the collet 118 or a twisting motion of a collet 118 once installed within the sleeve. The interlocks are formed by a protuberance 304a along one edge of a tang 28 and a complementary notch 304b in an adjacent tang 28. The base of the collet 118 further includes the annular lip 270 defining a stop for the sleeve 20. Along the outer peripheral edge of the annular lip 270, ribs 340 are located at 45° intervals from each other. The ribs 340 are essentially bulbous or circular in shape to provide concave edge surfaces for gripping to facilitate the threading procedure.

Figure 19:
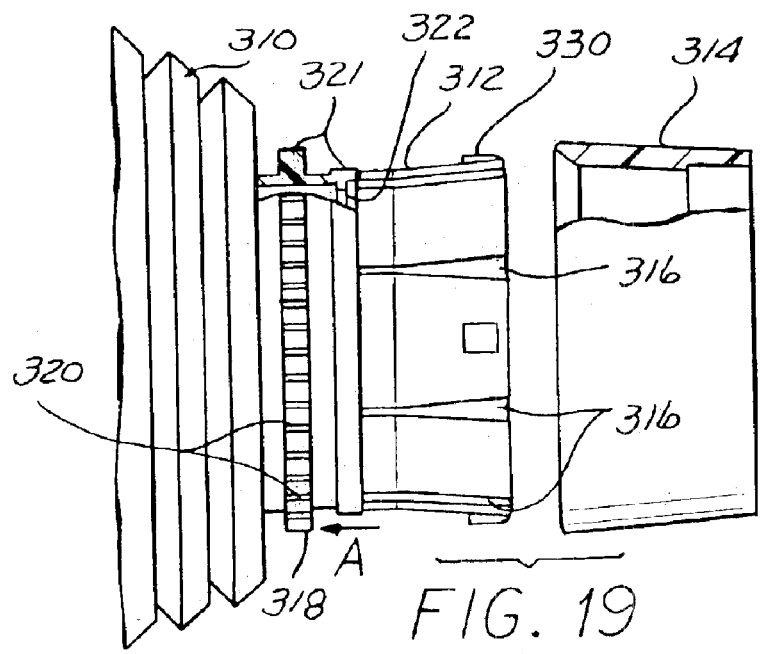
FIG. 19 is a side elevational view of another boot seal with an integral collet.
Figure 20:
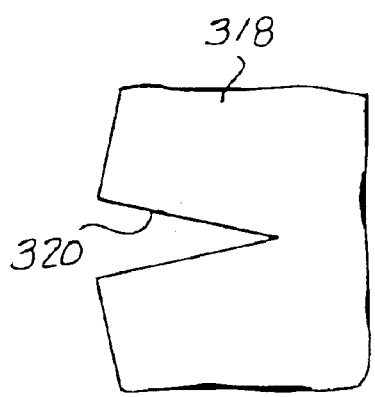
FIG. 20 is an enlarged elevational view of a micro slit taken along section A—A in FIG. 19.

FIG. 19 shows another boot 310 having an integral collet 312 for installation into a sleeve 314. The boot and the integral collet 310, 312, respectively, are made from a blow molded application. Therefore, rather than gaps to form the locking fingers as shown in FIG. 10, the gaps in FIG. 19 are actually webs 316 having a 0.030 millimeter thick material. The webs 316 are thin to allow the webs 316 to fold when the collet 312 is compressed within the sleeve 314. The webbed gaps 316 are only positioned along one end distal from the boot 310. Adjacent to the boot 310 is an annular ridge 318 having multiple micro slits 320 therein. FIG. 20 shows an enlarged view of one micro slit from the point of view of A of FIG. 19. The micro slits 320 allow the ridge 318 of the collet 312 to collapse to control the amount of compression the sleeve 314 exerts onto the retainer rings or shelves (not shown but located in the interior surface of the collet 312). Points of seal between the collet 312, sleeve 314, and tube 14 are located at 321 at retainer rings 318 and/or 322. This embodiment of this barb clamp will lock and seal flexible boot seals on any application regardless of shape or size. Such applications include air duct boots, front wheel drive boots and power steering boots.

Figure 21:
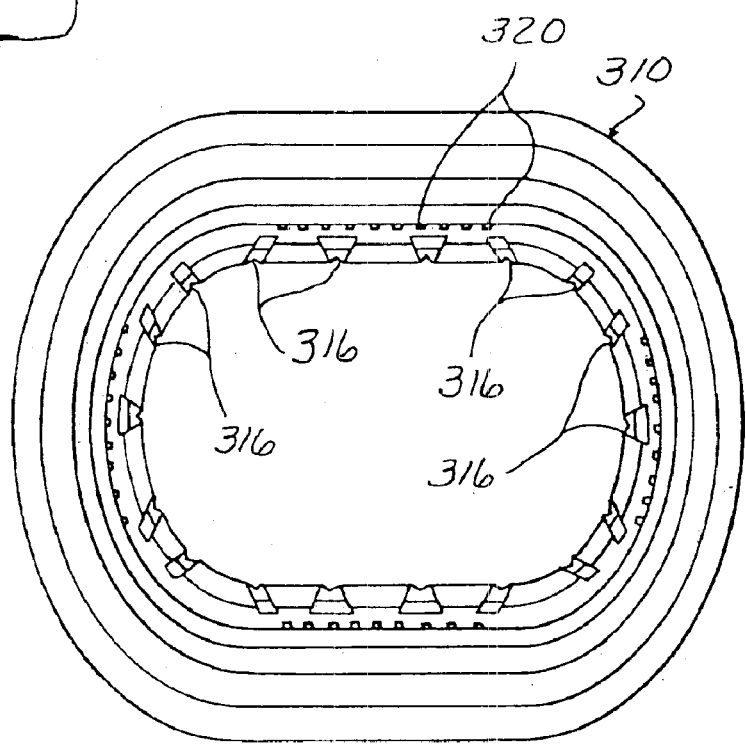
FIG. 21 is an end view of the boot seal and integral collet shown in FIG. 19.

FIG. 21 shows an end view of the boot 310 with integral collet 312 and illustrates the micro slits 320 and the webs 316. Further, FIG. 21 illustrates that the collet or the sleeve does not require a circular configuration but may be other configurations such as an oval, a polygon, etc. The collet 312 may include multiple retainer rings 318 and 322 on the collet 312. The micro slits 320 control the amount of compression the sleeve 314 exerts on the multiple retainer rings. The ledges or ramps 330 provide a stop means for the sleeve 314 when gripping against the shelf of the inner surface of the sleeve 34. This configuration of a boot having an integral collet provides many applications, including air duct boots, front wheel drive boots, and power steering boots as well as others.

Figure 22:
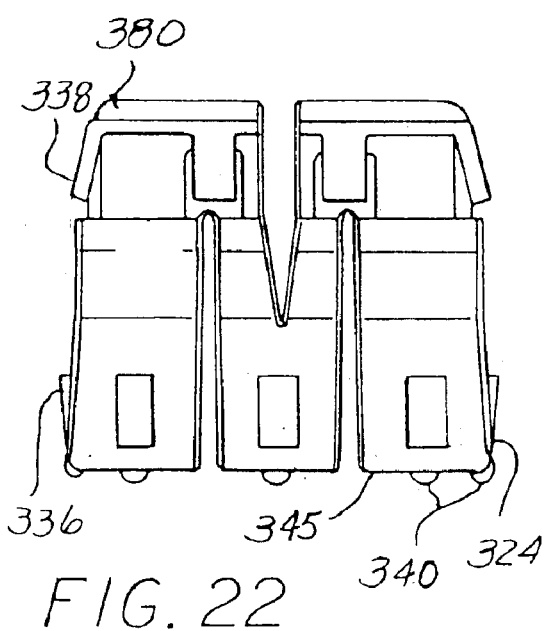
FIG. 22 is a side elevational sectional view of an embodiment of the collet having error proof features.
Figure 23:
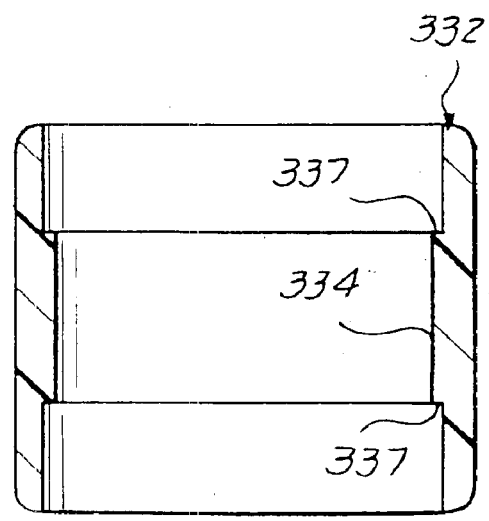
FIG. 23 is a side sectional view of an embodiment of the sleeve having error proof features.
Figure 24:
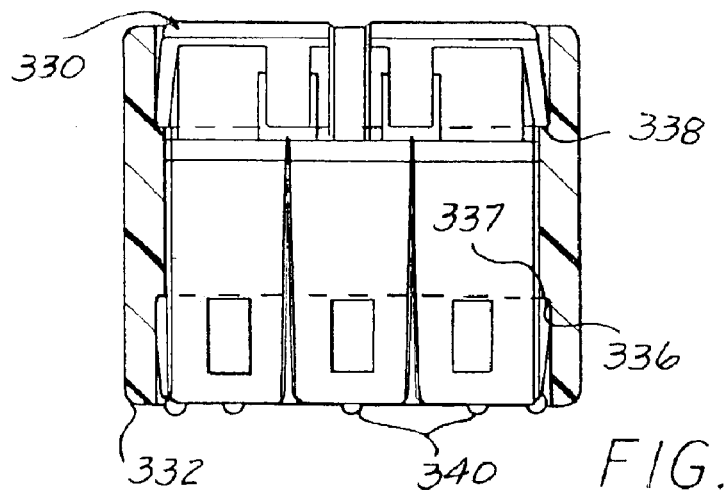
FIG. 24 is a side sectional view of the sleeve in FIG. 23 engaged over the collet in FIG. 22.

FIG. 22 shows a collet for use with an error proof sleeve shown in FIG. 23. FIG. 24 shows the sleeve 332 locked onto the collet 380. As can be seen in FIG. 23, the inner surface of the sleeve 332 has a centrally located reduced cross sectional area 334. The reduced cross-sectional area 334 is positioned equidistant from each end of the sleeve 332. The collet 380 shown in FIG. 22 is also configured and positioned such that the shelves 336 and ramps 338 will lock into the edges 337 of the reduced inner surface 334 of the sleeve 332. These configurations allow either end of the sleeve 332 to be moved over the collet 380. The collet 380 may include protuberances 340 in the shape of spheres or elongated modules 340 along the edge 324. The protuberances 340 help to facilitate the full travel of the collet during the assembly. As shown in FIG. 18, the protuberances 340 may be located along the radial stop 270.

Figure 25:
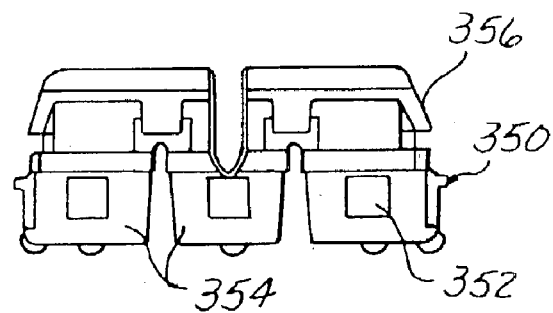
FIG. 25 is a side sectional view of an embodiment of a collet having only retaining features.
Figure 26:
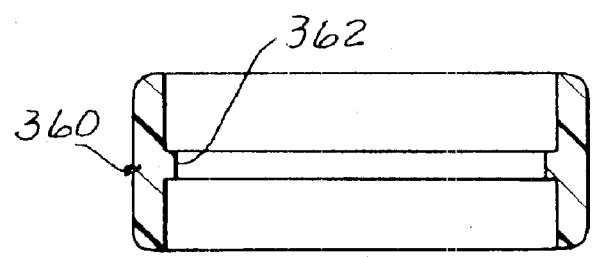
FIG. 26 is a side sectional view of an embodiment of a sleeve having only retaining features.
Figure 27:
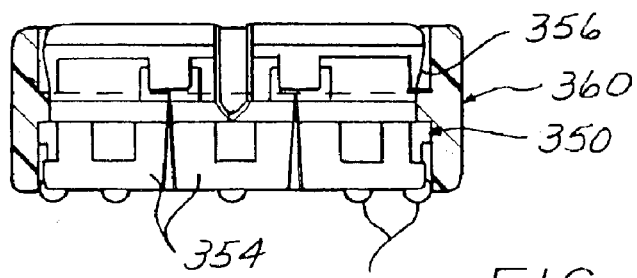
FIG. 27 is a side sectional view of the sleeves in FIG. 26 engaged over the collet in FIG. 25.

FIGS. 25, 26, and 27 show a retainer-only locking system for replacing a cable tie, hose clamp, and air clamps. FIG. 25 shows a collet 350 for the retainer only system. FIG. 26 shows a sleeve 360 for the retainer-only system. FIG. 21 shows the collet 350 and sleeve 360 assembled. In this embodiment a retainer only system retains hose and tubing but does not provide a 360° compression barb ridge. The retainer-only system has fixed ramps 352 on the locking fingers or tangs 354 and flexible ramps 356 on the upper portion of the collet 350. The flexible ramps 356 move inward during assembly and spring out to lock at final assembly to the inner surface ring 362 of the sleeve 360.

Figure 28:
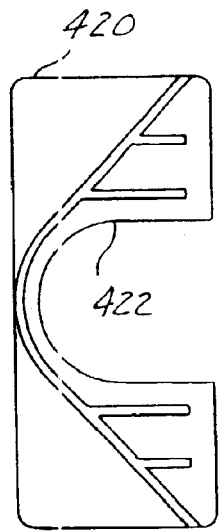
FIG. 28 is an end view of one component of an assembly device for the barb clamp.
Figure 30:
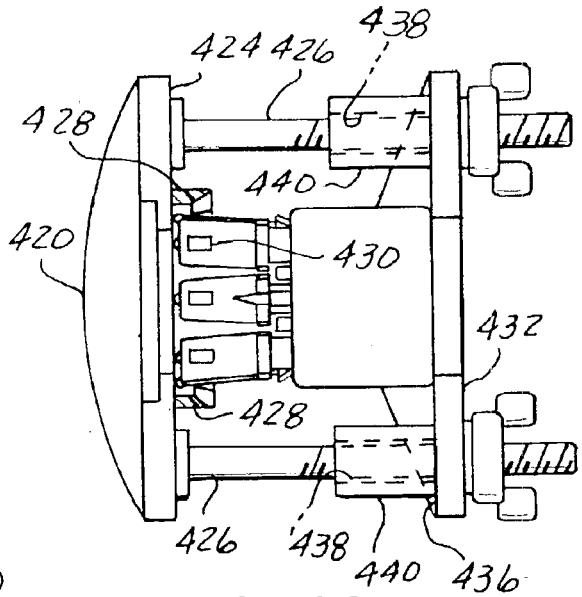
FIG. 30 is a side elevational view of a collet and sleeve in the assembly device.
Figure 29:
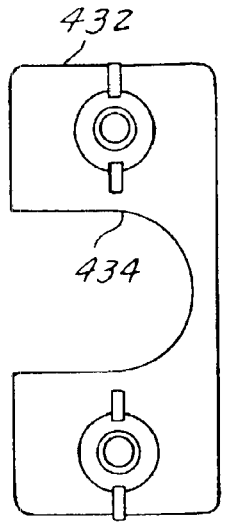
FIG. 29 is an end view of a second component of the assembly device for the barb clamp.

FIG. 28 shows a top plan view and FIG. 29 shows a bottom plan view of components for a tool for use by an individual consumer to lock a collet and sleeve assembly onto a tube and fitting. A common application would be for the use of repairing common garden hoses. FIG. 30 shows a side elevational view of the components of FIGS. 28 and 29 in use. The first component, hereinafter referred to as the top component 420, has a central slot 422 for receiving a portion of the fitting therethrough. The inner surface 424 of the first component 420 has a pair of dowels 426 extending from opposing sides of the first component 420. The inner surface 424 further has at least a pair of fingers 428 configured to grasp a collet at its base. The fingers 428 are preferably configured to latch or otherwise releasibly connect to the fixed ramps 430 of the collet.

The second component is best seen in FIGS. 29 and 30. The second component 432 has an interior slot 434 for receiving a portion of the tube therethrough. The interior surface 436 of the second component 232 has a pair of apertures 438 positioned for receiving the dowels 440 from the first component. The apertures 438 may be positioned within cylinders 440 attached by appropriate means to the inner surface of the second component 432. The collet and sleeve are positioned within the tool as shown in FIG. 30. The tool provides proper alignment of the sleeve with respect to the collet and the dowels 426 provide for axial alignment of the sleeve with respect to the collet. As the first and second components are brought together, the dowels 426 move within the aperture 438 as the collet is positioned within the sleeve.

Figure 31:
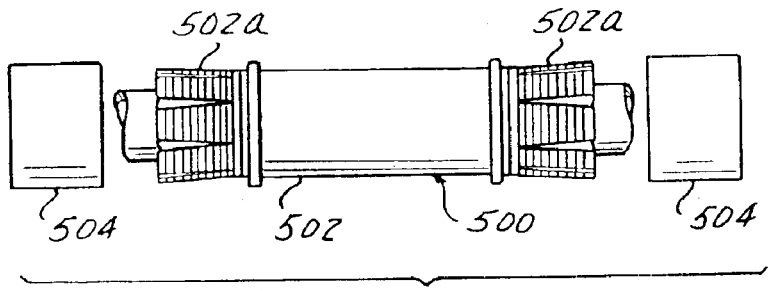
FIG. 31 is a side elevational view of a conductive coupling before being assembled.
Figure 32:
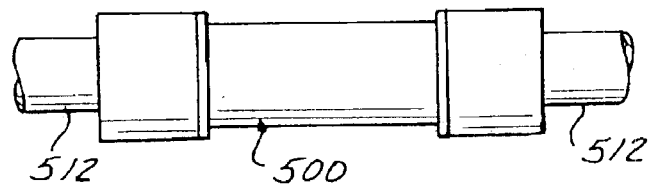
FIG. 32 is a side elevational view of the conductive coupling assembled.
Figure 33:
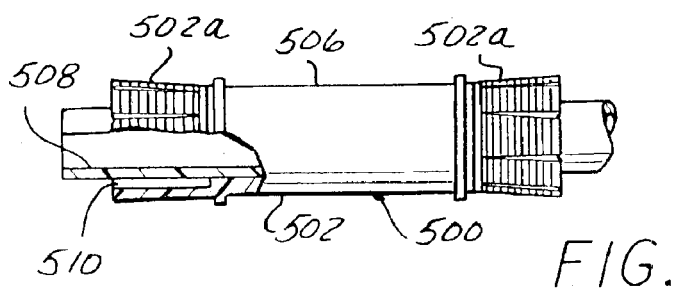
FIG. 33 is a partial cutaway view of the collet coupler component of the conductive coupling.

FIGS. 31–33 show a conductive coupling 500. Moving air, liquid, or powder through tubing, pipes, or conduit will generate static electricity. The conductive coupling is designed for earth grounding above and below ground. The conductive coupling includes a collet coupler 502 having a pair of collet members 502a attached at each end and at least one sleeve 504. The sleeves 504 are configured to have the same configuration of one of the previously described sleeves but is 50% thicker than the standard sleeve discussed supra to increase retention and provide additional protection against abrasion. Looking at FIG. 33 the collet coupler 502 is formed from an outer non-conductive plastic shell 506 having an inherently conductive polymer liner tube 508 therein. A space 510 is provided between the inherently conductive polymer liner 508 and the plastic collet coupler 502. The space 510 is configured to securely receive a conduit with a conductive liner 512. The conductive coupling 500 is assembled by first placing one sleeve 504 onto a conduit with a conductive liner 512. The free end of the conduit with the conductive liner 512 is slid into the space 512 of the collet coupler. The sleeve 504 is slid over the collet to lock the conduit with the conductive liner 512 within the space 510. The sleeve 504 secures the conduit and seals the conductive liner. The conductive coupling 500 may have a collet coupler formation at each end for coupling two separated conductive conduits together. Once the sleeves 504 are positioned and locked onto the collet portion of the collet coupler 502, through conductivity is provided from one side of the conductive coupling to the other side of the conductive coupling.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law. In addition, individual features shown on one embodiment may also be included on another embodiment. For example, the thread molded on the exterior surface of the collet shown in FIG. 18 may also be molded on other collets, such as on the collet members 502a of the conductive coupling 500. The protuberances 340 along the edge of the collet in FIGS. 18 and 22 may also be added to other embodiments of the collet. These and other features facilitate the assembly of the barb clamp and do not affect the dynamic retention and seal with a 360° radial compression of the barb clamp.

What is claimed is:

1. A barb clamp for securing a flexible tube to a tubular member with a barb fitting, the barb fitting having one end insertable into the tube, the barb clamp comprising:
   a cylindrical collet engageable over the one end of the tubular member and tube; and
   a cylindrical sleeve having a through center aperture for receiving and locking said collet therein, wherein the collet has a plurality of resilient means radially spaced by V-shaped gaps and has an exterior surface with an annular groove in the exterior surface and has an annular lip radially extending from one end for defining a stop for the sleeve and wherein said sleeve has an interior surface with an annular projection configured and positioned for disposition in the annular groove of the collet, and said plurality of resilient means radially contract around the tube and substantially eliminate the V-shaped gaps for providing a 360° compression around the tube when the collet is locked in the sleeve.

2. The barb clamp of claim 1 further comprising a thread molded into a portion of the exterior surface of the collet.

3. The barb clamp of claim 1, wherein the collet is integrally molded to the sleeve, wherein the collet is connected to the sleeve at thin frangible pieces of plastic.

4. The barb clamp of claim 1, wherein the collet is integrally molded to a boot having a corrugated exterior portion and wherein the annular lip is located between the collet and boot.

5. The barb clamp of claim 4, wherein the annular lip is a ridge having micro slits formed therein.

6. The barb clamp of claim 4, wherein the wherein the resilient means includes a plurality of tangs which flare outwardly at the end, wherein each tang is connected to another radially spaced tang by a web formed by a piece of foldable plastic material.

7. The barb clamp of claim 1, wherein the collet has an annular bulge at a middle portion of the exterior surface for gripping an inner surface of the sleeve.

8. The barb clamp of claim 7, wherein the sleeve has a reduced inner bore positioned for tightly receiving the annular bulge of the collet to provide superior holding strength for the tube and barb fitting.

9. The barb clamp of claim 8, wherein the collet is integrally molded to the sleeve, and wherein the collet is connected to the sleeve by frangible pieces of plastic.

10. The barb clamp of claim 1, wherein the tube has a corrugated portion and the interior surface of the sleeve has a ridged portion to correspond with the corrugated portion of the tube.

11. The barb clamp of claim 1, wherein the exterior surface of the collet has one end surface with protuberances projecting therefrom for facilitating the full travel of the collet during assembly.

12. The barb clamp of claim 1, wherein the collet is a collet coupler formed from an outer non-conductive plastic shell and an inherently conductive polymer liner tube therein with a pair of collet members attached at each end, wherein there is a space between the inherently conductive polymer liner and plastic collet shell for receiving the tube at one end and the tubular member at the other end.

13. The barb clamp of claim 1, wherein the collet has fixed locking ramps on the resilient means and and the sleeve has an annular projection on an inner surface wherein the fixed locking ramps click into a final locking position with the annular projection on assembly.

14. The barb clamp of claim 13, further comprising protuberances located on an exterior bottom edge of the collet.

15. A barb clamp for securing a flexible tube to a tubular member having a barb fitting at one end, said barb fitting insertable into the tube, the barb clamp comprising:

a cylindrical collet engageable over the one end of the tubular member and tube; and a cylindrical sleeve having a through center aperture for receiving and locking said collet therein, wherein the collet is integrally molded to the sleeve and connected to the sleeve with thin frangible pieces of plastic, and wherein said collet has an exterior surface and an annular groove in the exterior surface proximate to the first end of the collet, and the exterior surface having a plurality of ledges extending therefrom and further having resilient means formed by V-shaped through slots extending from one end of the collet, wherein the ledges are positioned adjacent the annular groove for providing a stop for the sleeve and the resilient means providing a 360° compression around the tube when the collet is locked in the sleeve.

16. The barb clamp of claim 15 further comprising a thread molded into a portion of the exterior surface of the collet.

17. The barb clamp of claim 15 wherein the collet has an annular lip at one end.

18. The barb clamp of claim 15, wherein the collet has a retainer ring on an interior surfaces of the resilient means.

19. The barb clamp of claim 15, wherein the collet further includes interlocks on the annular lip for preventing a twisting motion of the collet when locked in the sleeve.

20. The barb clamp of claim 15, wherein the barb fitting has a barbed configuration at one end and the collet has an interior surface with an annular shelf extending therefrom positioned for locking under the barb configuration of the barb fitting.

* * * * *